United States Patent [19]

van der Stegen et al.

[11] 4,364,965

[45] Dec. 21, 1982

[54] PROCESS FOR EXTRACTING CAFFEINE FROM SOLUTIONS THEREOF IN CARBON DIOXIDE UNDER HIGH PRESSURE

[75] Inventors: Gerrit H. D. van der Stegen, Montfoort; Hendricus G. J. de Wilt, Zaltbommel, both of Netherlands

[73] Assignee: D.E.J. International Research Company B.V., Utricht, Netherlands

[21] Appl. No.: 182,715

[22] Filed: Aug. 29, 1980

Related U.S. Application Data

[63] Continuation of Ser. No. 958,666, Nov. 8, 1978, abandoned.

[30] Foreign Application Priority Data

Nov. 14, 1977 [NL] Netherlands ......................... 7712503

[51] Int. Cl.$^3$ .............................................. A23F 5/20
[52] U.S. Cl. .................................... 426/481; 426/427; 544/274

[58] Field of Search .................. 426/427, 481; 544/274

[56] References Cited

U.S. PATENT DOCUMENTS 3,879,569  4/1975  Vetzbum et al. .................... 426/427
4,031,251  6/1977  Margolis ......................... 426/427 X

FOREIGN PATENT DOCUMENTS 7708374  2/1978  Netherlands ......................... 426/427
1488340  10/1977  United Kingdom ................ 426/427

*Primary Examiner*—Joseph M. Golian
*Attorney, Agent, or Firm*—Cushman, Darby & Cushman

[57] ABSTRACT

Extraction of caffeine from solutions thereof is accomplished with carbon dioxide under high pressure, using adsorbents which combine a high adsorption capacity for caffeine with such hydrophilic properties that the caffeine-laden adsorbent can be regenerated using water only.

10 Claims, No Drawings

PROCESS FOR EXTRACTING CAFFEINE FROM SOLUTIONS THEREOF IN CARBON DIOXIDE UNDER HIGH PRESSURE

CROSS-REFERENCE TO RELATED APPLICATIONS

This application is a continuation of our earlier application Ser. No. 958,666 filed Nov. 8, 1978 and now abandoned.

For the decaffeination of green coffee beans, various processes have been proposed, in which the caffeine is taken up in carbon dioxide under high pressure. It has also been proposed to recover the caffeine from the carbon dioxide solution by means of adsorbents.

The present invention relates to a process for the extraction of caffeine from solutions thereof in carbon dioxide under high pressure. According to the invention, this process is characterized in that caffeine is extracted from the carbon dioxide solution by means of synthetic adsorbents which combine a high adsorption capacity for caffeine, preferably of more than 25 g/kg, with such hydrophilic properties that regeneration of the adsorbent laden with caffeine is possible by using exclusively water.

Preferred synthetic adsorbents for use in the process according to the present invention are synthetic polymeric resins with an adsorbent surface having an aromatic character, in which the hydrophobic properties inherent in such aromatic character are suppressed by the presence of a polar, very weakly ionic, acidic group derived from monomers having a $p_K$ value of more than 7, such as phenol, anisol and naphthol.

In a preferred embodiment of the process according to the present invention, use is made of synthetic polymeric resins produced by polymerization or copolymerization of monomers containing aromatic ring systems and acidic groups such that the ratio of the total molar adsorption capacity for caffeine (number of moles of caffeine adsorbed per kg resin to complete saturation) to the total number of acidic groups (expressed as acid equivalents per kg resin) ranges from 1 to 25, in particular from 5 to 15. As regards the polymerization of the above monomers, reference may be had to British Pat. No. 573,116 and to Ind. Eng. Chem. 51 (1959) 759–762.

The presence of the groups referred to gives the resin a hydrophilic character, as a result of which a good wetability is obtained, and the resin also becomes regeneratable with water. As the groups are so weakly ionic, under the process conditions, in particular at the prevailing degree of acidity, there is virtually no ion exchange, as is the case in the process described in German Offenlegungsschrift No. 2,637,197. This has the advantage that practically no foreign ions are introduced into the green coffee or into the green coffee extract (prevailing pH: 5–6) and also that the regeneration of the adsorbent does not require the use of electrolytes. The adsorption is evidently accomplished by the aromatic ring systems present in the resin.

One example of a commercially available adsorbent which has been found to be particularly suitable for the purposes of the present invention is Duolite S761, a formol phenol resin of the firm of Diaprozim.

The present invention also relates to a process for decaffeinating green coffee, which in one embodiment comprises the following steps:

- wetting the green coffee with water and/or steam to 30–60%;
- extracting the caffeine from the wetted coffee by means of $CO_2$ saturated with water under high pressure (200–400 ats; 20.3–40.5 MPa);
- passing the caffeine-laden $CO_2$ phase over the adsorbent (saturated with water), preferably under isobaric conditions, and thereafter recycling the $CO_2$ phase liberated from caffeine for re-use for extraction of green coffee;
- regenerating the laden adsorbent with water of 50°–100° C., and thereafter re-using the adsorbent, and treating the aqueous caffeine solution in known manner to recover pure caffeine;
- drying the caffeine-free, still wet green coffee, after removal from the $CO_2$ system, to its original moisture content, preferably in a stream of air at a temperature below 100° C.

According to a different embodiment of the process according to the invention for decaffeinating green coffee, the green coffee is treated in known manner (see for example U.S. Pat. No. 2,309,092) with an aqueous extract of green coffee, whereafter caffeine is removed from the resulting aqueous extract in known manner (see for example German Offenlegungsschriften Nos. 2,357,590 and 2,638,383) by means of wet $CO_2$ under high pressure. The caffeine-laden $CO_2$ phase is then stripped of caffeine by means of an adsorbent in the manner described hereinbefore.

In a third embodiment of the process according to the invention for decaffeinating green coffee, the coffee beans are mixed with the adsorbent in one bed, which is bodily subjected to a $CO_2$ atmosphere of 20.3–40.5 MPa (200–400 ats). Preferably there is forced circulation of $CO_2$. After completion of the adsorption process, the coffee beans must of course be separated from the adsorbent.

A study of the distribution co-efficients for caffeine in the moist green coffee/wet $CO_2$ and wet $CO_2$/wet Duolite S 761 systems taught that there are surprising temperature optima in the process, namely,

- a double optimum for moist coffee/wet $CO_2$, namely, 20°–30° C. and 60°–90° C.;
- one optimum for wet $CO_2$/wet adsorbent of 30°–60° C., which range, however, is not very critical as the distribution co-efficient also has a favourable value outside this range, so that isothermic operation under the conditions of the double optimum is quite feasible. Duolite S-761 (Diamond Shamrock) is a macroporous adsorbent resin having hydroxyl groups with a phenolic matrix. The adsorbent resin is highly porous, resistant to attrition, regenerated with alkali and is a very weak acid resin.

EXAMPLE 10 kg green coffee is moistened with wet steam of approximately 152 kPa (1.5 ats) to a moisture content of 45–55%. The coffee thus moistened is extracted over a period of 8–12 hours in 6 equilibrium steps with a total quantity of approximately 750 kg/$CO_2$ at a temperature of 75° C. and a pressure of 25.3 MPa (250 ats). Thereafter the $CO_2$ is passed over 10 kg of the adsorbent Duolite S 761 (which has been adjusted to a moisture content of 60–70% with water) at a temperature of 75° C. and a pressure of 25.3 MPa (250 ats), whereby it is stripped of caffeine in 5 equilibrium steps. The resulting decaffeinated coffee has a residual caffeine content of less than 0.07%, calculated on the dry solids. The $CO_2$ stripped of caffeine can be reused for the extraction of green coffee, and, after regeneration with water, the adsorbent is again suitable for stripping caffeine-laden $CO_2$ of caffeine.

We claim:

1. A process for decaffeinating green coffee beans without introducing foreign ions into the green coffee beans or green coffee extract, said process comprising the steps of:
   (a) adjusting the moisture content of the green coffee beans to a value of from about 30 to about 60% by weight;
   (b) passing water-saturated carbon dioxide through said green coffee beans under a high pressure of about 20.3 to about 40.5 MPa and extracting caffeine from the moistened coffee beans;
   (c) contacting the caffeine-containing carbon dioxide gas stream of step (b) with a macroporous synthetic polymer resin adsorbent,
   said resin produced by the polymerization or copolymerization of monomers containing aromatic ring systems and polar acidic groups having a $P_K$ value greater than 7, and wherein
   the ratio in said resin of the total molar adsorption capacity for caffeine, expressed as the number of moles of caffeine adsorbed per kg of resin, to complete saturation, to the total number of acidic groups, expressed as acid equivalents per kg of resin, is between 1 and 25,
   thereby adsorbing and removing the caffeine from the caffeine-laden carbon dioxide gas stream;
   (d) returning the carbon dioxide stream of step (c) to step (b) for reuse;
   (e) regenerating the caffeine-laden adsorbent of step (c) by contacting said resin with water as the sole regenerating material at a temperature in the range of about 50° to about 100° C.;
   (f) reusing the regenerated resin from step (e) in step (c); and thereafter
   (g) recovering and drying the decaffeinated green coffee product.

2. A process according to claim 1, wherein the ratio ranges from 5 to 15.

3. The process of claim 1 wherein the moist coffee beans are at a temperature of about 20° C. to about 30° C. when contacted with the saturated carbon dioxide of step (b) and wherein step (b) is conducted at a temperature of about 50° C. to about 90° C.

4. The process of claim 1 or 3 wherein said adsorbent resin is a highly porous, very weak-acid resin having a phenolic matrix.

5. A process for extracting caffeine from a solution thereof in carbon dioxide with an adsorbent and regenerating the adsorbent with water, said process comprising the steps of:
   (1) contacting a caffeine-laden carbon dioxide stream under high pressure with a macroporous synthetic polymer resin adsorbent produced by polymerizing a monomer containing aromatic ring systems and polar acidic groups having a $P_K$ value greater than 7 and wherein the ratio of the total molar adsorption capacity for said caffeine, expressed as the number of moles of caffeine adsorbed to complete saturation per kg resin, to the total number of acidic groups, expressed as acid equivalents per kg resin, is from 1 to 25, and thereafter
   (2) regenerating the caffeine-laden resin adsorbent by contacting it with water as the sole regenerating means and removing the adsorbed caffeine from said resin.

6. The process of claim 5 wherein said adsorbent resin is a highly porous, very weak-acid resin having a phenolic matrix.

7. The process of claim 5 wherein said ratio is from 5 to 15.

8. The process according to claim 5, 6 or 7 wherein said synthetic polymeric resin has an adsorbent surface with an aromatic character, and wherein the hydrophobic properties inherent in such aromatic character are suppressed by the presence of a polar, very weakly ionic acidic groups derived from said monomers having a $P_K$ value greater than 7.

9. The process of claim 1 or 5 wherein said monomer having a $P_K$ value greater than 7 is selected from the group consisting of phenol, anisol and naphthol.

10. A process for decaffeinating green coffee beans to produce a substantially caffeine-free green coffee extract without introducing foreign ions into the green coffee beans or green coffee extract, said process comprising the steps of:
    (a) adjusting the moisture content of the green coffee beans to a value of from about 30 to about 60% by weight;
    (b) passing water-saturated carbon dioxide through said green coffee beans under a high pressure of about 20.3 to about 40.5 MPa and extracting caffeine from the moistened coffee beans;
    (c) contacting the caffeine-containing carbon dioxide gas stream of step (b) with a macroporous synthetic polymer resin adsorbent,
    said resin is a highly porous, very weak-acid resin having a phenolic matrix, produced by the polymerization or copolymerization of monomers containing aromatic ring systems and polar acidic groups having a $P_K$ value greater than 7, and wherein
    the ratio in said resin of the total molar adsorption capacity for caffeine, expressed as the number of moles of caffeine adsorbed per kg of resin, to complete saturation, to the total number of acidic groups, expressed as acid equivalents per kg of resin, is between 1 and 25, thereby adsorbing and removing the caffeine from the caffeine-laden carbon dioxide gas stream;
    (d) returning the carbon dioxide stream of step (c) to step (b) for reuse;
    (e) regenerating the caffeine-laden adsorbent of step (c) by contacting said resin with water as the sole regenerating material at a temperature in the range of about 50° to about 100° C.;
    (f) reusing the regenerated resin from step (e) in step (c); and thereafter
    (g) recovering and drying the decaffeinated green coffee product.

* * * * *